United States Patent
Noecker et al.

(10) Patent No.: US 7,160,334 B2
(45) Date of Patent: Jan. 9, 2007

(54) COMPOSITION FOR BLEACHING HUMAN HAIR

(75) Inventors: Bernd Noecker, Ober-Ramstadt (DE); Katrin Blumenschein, Brombachtal-Heubach (DE)

(73) Assignee: KPSS-Kao Professional Salon Services GmbH, Darmstadt (DE)

( * ) Notice: Subject to any disclaimer, the term of this patent is extended or adjusted under 35 U.S.C. 154(b) by 339 days.

(21) Appl. No.: 10/866,019

(22) Filed: Jun. 10, 2004

(65) Prior Publication Data

US 2005/0097683 A1    May 12, 2005

(30) Foreign Application Priority Data

Jul. 3, 2003    (EP) .................... 03015057

(51) Int. Cl.
*D06L 3/00*    (2006.01)
(52) U.S. Cl. ............... 8/101; 8/107; 8/111; 514/625; 568/337
(58) Field of Classification Search ............ 8/101, 8/107, 111; 514/625; 568/337
See application file for complete search history.

(56) References Cited

FOREIGN PATENT DOCUMENTS

| DE | 197 51 550 A1 | 7/1999 |
|---|---|---|
| DE | 101 50 742 A1 | 4/2003 |
| EP | 1 269 976 A2 | 1/2003 |
| EP | 1269 976 A2 * | 1/2003 |

OTHER PUBLICATIONS

R.C. Pepe, J.A. Wenninger, G.N. Mcewen: "International Cosmetic Ingredient Dictionary and Handbook, Ninth Edition" 2002, The Cosmetic, Toiletry, and Fragrance Association, Washington D.C> XP002263138 1, p. 309.
European Search Report for application No. EP 03 01 5057 dated Dec. 19, 2003.

* cited by examiner

*Primary Examiner*—Eisa Elhilo
(74) *Attorney, Agent, or Firm*—Norris McLaughlin & Marcus PA

(57) ABSTRACT

A water-free composition for the bleaching and brightening of human hair at the same time with a simultaneous conditioning effect is disclosed. The particularly exceptional effects of the bleaching agent is that improvement of shine and elasticity. The bleaching agent comprises
a) at least one compound with a bleaching or brightening effect, in particular a peroxide and/or an ammonium salt, and
b) 0.001% to 10% by weight, calculated to the total composition, of at least one ubiquinone of the formula (I)

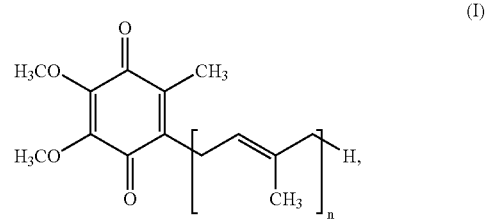

wherein n is a number from 1 to 10, and
at least one sphingolipid of the formula II

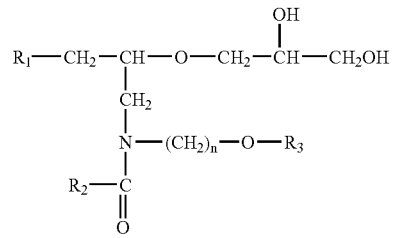

where $R^1$ and $R^2$ are independent from each other alkyl- or alkenyl group mit 10 to 22 carbon atoms, $R^3$ is methyl, ethyl, n-propyl or isopropyl group and n is a number between 1 to 6, preferably 2 or 3.

8 Claims, No Drawings

COMPOSITION FOR BLEACHING HUMAN HAIR

The present invention concerns a new composition for the intensive, yet gentle bleaching and brightening of human hair with improved shine effect and obviously less damaging.

The bleaching of human hair customarily consists of a process with the following steps:

Homogenous mixing of a water-free preparation, preferably a powder, comprising at least one compound with a bleaching or brightening effect, in particular a solid peroxide salt, preferably ammonium, potassium and/or sodium persulfate or earth alkali peroxide, with an aqueous hydrogen peroxide solution, application of this composition onto the hair, and rinsing after bleaching is completed. However, it has been known for some time that use of those components effective with regard to the bleaching, in particular the persulfates, especially the ammonium persulfate, in the requisite higher concentrations can lead to hair damage.

Efforts have already been made to solve this problem by (partial) substitution of the persulfates, however, so far the results have not been satisfactory.

Earlier it has been reported in EP 1 269 976, that addition of ubiquinone reduces hair damage and also improves wet and dry combability, texture and volume of hair.

It has now been found, and it is the object of the present invention, that addition of sphingolipid into ubiquinone containing bleaching compositions comprising anhydrous substances, in particular peroxides, as agents, surprisingly not only achieves an improved bleaching effect without causing major hair damage, it also improves the properties of the hair thus treated, in particular shine and elasticity of hair in addition to wet and dry combability, and volume of the hair.

Object of the invention is also a process for the bleaching of human hair with a preparation obtained by mixing a water-free composition (A), comprising at least a one compound with a bleaching or brightening effect, preferably a peroxide with an aqueous hydrogen peroxide composition (B).

This task is solved by the addition of 0.001% to 10% by weight, calculated to the total composition, of at least one ubiquinone of the formula (I)

$$\text{(I)}$$

wherein n is a number from 1 to 10, and a sphingolipid of the following formula II at a concentration of 0.001% to 10% by weight, calculated to the total composition, $$\text{(II)}$$

where $R^1$ and $R^2$ are independent from each other alkyl- or alkenyl group mit 10 to 22 carbon atoms, $R^3$ is methyl, ethyl, n-propyl or isopropyl group and n is a number between 1 to 6, preferably 2 or 3.

Preferred ubiquinone are those with n=6 to 10, in particular ubiquinone 50, wherein n stands for 10, also known by the name "Coenzyme Q 10".

The preferred sphingolipid represented by the formula II is cetyl-PG hydroxyethyl palmitamide The use of "Coenzyme Q 10" in cosmetic compositions, in particular in hair conditioning compositions, is known per se.

EP 0 751 762 B describes hair conditioning compositions comprising one or more ubiquinones, in particular coenzyme Q 6 and coenzyme Q 10, in combination with retinols, retinals and β-carotin, for the treatment of ageing skin.

Styling compositions on aqueous basis comprising one or more bioquinones such as ubiquinones and plastoquinones for protection of the scalp and hair against undesired oxidation processes are known from DE 199 26 167 A1.

DE 199 26 168 A1 discloses styling compositions on alcoholic basis with bioquinones, in particular coenzyme Q 10.

DE 199 26 170 A1 concerns the use of one or more bioquinones such as ubiquinone in cosmetic hair cleansing compositions.

Finally, DE 199 26 156 A1 describes the use of bioquinones such as ubiquinone for the preparation of cosmetic compositions for improving the hair structure, in particular combability of the hair, i.e. hair-conditioning compositions.

EP 857 052 B1 describes sphingolipids or ceramides in oxidizing composition and especially in a permanent shaping process wherin hair is first treated with a reducing composition.

DE 197 51 550 describes the use of sphingolipid of the formula II in hair care preparations.

In view of this state of the art, the improved bleaching effect and at the same time improved elasticity and shine provided by the addition of ubiquinones and sphingolipids to bleaching compositions was not to be expected, in particular in the event of application onto previously damaged hair.

The preferred use concentrations of the coenzymes Q 1 to Q 10 ranges from about 0.005% to 5%, in particular about 0.01% to 2.5%, especially preferred about 0.05% to 1% by weight, calculated to the total bleaching powder composition (excluding the oxidation agent).

The preferred use concentrations of the spingolipids of the formula II ranges from about 0.005% to 5%, in particular about 0.01% to 2.5%, especially preferred about 0.01% to 1% by weight, calculated to the total bleaching powder composition (excluding the oxidation agent).

According to a preferred embodiment of the invention, the bleaching and brightening powders are used as dust-free products present as granules or agglomerates.

These can, for example, be those products disclosed in EP-A 560 088, which contain an oil or a liquid wax, whereby application of this oil or wax is preferably carried out in a spraying process.

According to the invention, it is also possible to use dust-free bleaching powders prepared according to EP-A 630 643 by agglomerating the initially pulverulent components by spraying onto these molten waxes or $C_{10}$–$C_{18}$-fatty acid alkanolamides, or by melting the same together at increased temperatures.

In addition to the active component, the bleaching agent compositions also contain the components customarily used in such compositions.

In the event the preparation is a powder, in particular inert pulverulent carrier materials, these are for example, pyrogenic silicon dioxide, starch powder, etc., alkalizing agents, such as sodium metasilicate, surface-active substances, binding agents, etc. In order to avoid repetition, reference is made to the respective standard literature, for example, K. Schrader, "Grundlagen und Rezepturen der Kosmetika", $2^{nd}$ Ed. (1989, Huthig Buchverlag), pages 815 to 823.

Peroxides are used as active components. Useful as such are in particular persulfates such as sodium and potassium persulfate, ammonium persulfate, earth alkali peroxides such as magnesium peroxide, melamine peroxide or urea peroxide or phtholimidoperoxy-hexanoic acid.

The proportion of peroxides is at least 10%, preferably at least 20% to about 80%, calculated to the total composition.

According to a preferred embodiment of the invention, the bleaching compositions can also comprise 0.1% to 10% by weight, calculated to the total composition, of one or more ammonium salts.

Suitable ammonium salts are ammonium carbonate, ammonium hydrogen carbonate, ammonium carbamate, ammonium chloride, ammonium sulfate, ammonium phosphates, ammonium nitrate, ammonium bromide, ammonium iodide, ammonium thiosulfate, ammonium molybdate, ammonium vanadate, ammonium sulfamate, ammonium citrate, ammonium salicylate, ammonium valerate, ammonium artrate, ammonium benzoate, ammonium acetate, ammonium formiate and ammonium lactate.

Preferred thereof are the ammonium phosphates, such as $NH_4H_2PO_4$, $(NH_4)_2HPO_4$, $(NH_4)_2NaPO_4$, $NaNH_4HPO_4$ or $NH_4Na_2PO_4$, ammonium chloride, ammonium sulfate and diammonium hydrogen citrate, as well as ammonium chloride, preferably in an amount from 0.1% to 10% by weight, calculated to the total composition.

As known from EP 609 796 A2, the ammonium compounds can also be used as sole bleaching agent in respectively higher amounts.

The proportion of the bleaching or brightening compounds in total preferably ranges from about 5% to about 75%, in particular about 25% and about 60% by weight, in reference to the brightening and bleaching powder.

The particle sizes of the bleaching compositions according to the invention generally range below 1 mm, preferably below 500 microns, for example, less than 400 microns, in particular about 25 to about 100 μm, thus ensuring excellent processing capability, i.e. mixability with an aqueous hydrogen peroxide solution prior to application onto human hair.

Application of the composition is carried out in the customary manner known per se. The pulverulent brightening composition is mixed homogenously with a 6 percent to 12 percent hydrogen peroxide solution, preferably in a proportion of about one part by weight of the powder to about 0.5 to about 4 parts, in particular about 1 part to about 2.5 parts by weight of the peroxide solution or lotion, and subsequently left on the hair to process for about 10 to about 60 minutes, in particular about 20 to 30 minutes, depending on the temperature.

Application may also be carried out in a manner wherein the bleaching powder and the hydrogen peroxide solution are mixed with a cream base, this homogenous mixture then being applied onto the hair.

The composition is preferably adjusted at such levels that upon admixture with the aqueous hydrogen peroxide solution, it achieves a pH-value of about 8 to about 11.5, in particular between 9 and 11 in the ready-to-use mixture.

The following Examples illustrate the invention.

EXAMPLE 1 a) Brightening Powder

| | |
|---|---|
| Silicon dioxide | 16.17 (% by wt.) |
| Ammonium chloride | 14.70 |
| Sodium carbonate | 10.00 |
| Sodium metasilicate | 2.30 |
| Phthalimidoperoxyhexanic acid | 41.50 |
| Sodium persulfate | 15.20 |
| Coenzyme Q 6 | 0.03 |
| Cetyl PG hydroxyethyl palmitamide | 0.10 |

This composition is mixed in a weight proportion of 1:2.5:2.5 with an $H_2O_2$ lotion b) and a cream base c):

b) Hydrogen Peroxide Lotion

| | |
|---|---|
| Hydrogen peroxide | 6.00 (% by wt.) |
| Cetyl stearyl alcohol | 1.70 |
| Phosphoric acid | 0.50 |
| Sodium lauryl sulfate | 0.20 |
| Coenzyme Q 6 | 0.05 |
| Cetyl PG hydroxyethyl palmitamide | 0.10 |
| Disodium hydrogen phosphate | 0.10 |
| Salicylic acid | 0.10 |
| Water | ad 100.00 | c) Cream Base

| | |
|---|---|
| Cetyl stearyl alcohol | 11.0 (% by wt.) |
| Oleth-5 | 5.0 |
| Oleic acid | 2.5 |
| Stearamide MEA | 2.3 |
| Cocoamide MEA | 2.3 |
| Sodium cetyl stearyl sulfate | 1.2 |
| 1.2-Propyleneglycol | 1.0 |
| 1.2-Propyleneglycol stearate | 0.6 |
| Sodium lauryl sulfate | 0.5 |
| Wheat protein hydrolyzate | 0.9 |
| Organopolysiloxane | 0.4 |
| Cetyl PG hydroxyethyl palmitamide | 0.1 |
| Panthenol | 0.6 |
| Perfume | 0.4 |
| Complexing agent | 0.2 |
| Water | ad 100.0 |

The pH-value of this mixture was 9.0.

Upon application this mixture showed an excellent, even bleaching effect with good wet and dry combability and excellent gloss, and improved elasticity; substantial hair damage was not apparent on strands of undamaged human hair.

Omission of the "Coenzyme Q 6" and cetyl PG hydroxyethyl palmitamide in the compositions led to a reduced, less even bleaching effect and reduced conditioning of the hair. Hair had less elasticity and less shine.

EXAMPLE 2

Bleaching Powder

| | |
|---|---|
| Kieselguhr | 2.60 (% by wt.) |
| Sodium carboxymethyl cellulose | 2.50 |
| Hydroxyethyl cellulose | 1.60 |
| Sodium lauryl sulfate | 2.50 |
| Sodium stearate | 1.60 |
| Protein hydrolyzate | 0.60 |
| Starch | 1.00 |
| Sodium carbonate | 0.60 |
| Sodium metasilicate | 9.00 |
| Polyvinyl pyrrolidone K90 | 3.20 |
| Coco fatty acid monoethanolamide | 9.80 |
| $(NH_4)_2HPO_4$ | 2.00 |
| Magnesium peroxide | 3.80 |
| Potassium persulfate | 8.00 |
| Sodium persulfate | 50.00 |
| Organopolysiloxane | 1.00 |

| Bleaching Powder | |
|---|---|
| Coenzyme Q 10 | 0.20 |
| Cetyl PG hydroxyethyl palmitamide | 0.10 |

A dust-free powder is obtained, which shows good capabilities of being mixed with a known 6% $H_2O_2$-solution in a weight proportion of 1:1.

The pH-value of this mixture is 9.0.

Upon application, this mixture also showed an excellent, even bleaching effect with good wet and dry combability and excellent gloss; substantial hair damage did not appear on strands of undamaged human hair. Elasticity of hair is enhanced as well dramatically.

Omission of the "Coenzyme Q 10" and cetyl PG hydroxyethyl palmitamide resulted in a clearly reduced bleaching effect and hair is appeared to be dull and at the same time do not have any elasticity. Consequently, no volume and style hold could be achieved.

EXAMPLE 3

| Dust-Free Bleaching Powder | |
|---|---|
| Silicon dioxide (diatomaceous earth) | 3.20 (% by wt.) |
| Silicon dioxide (pyrogenic $SiO_2$) | 5.25 |
| Sodium carboxymethyl cellulose | 3.50 |
| Urea | 2.00 |
| Sodium lauroyl sarcosinate | 0.80 |
| Sodium stearate | 1.20 |
| Sodium carbonate | 1.00 |
| Sodium metasilicate | 6.00 |
| Starch powder | 3.50 |
| Potassium persulfate | 57.00 |
| Magnesium peroxide | 4.00 |
| Organopolysiloxane | 1.00 |
| Coenzyme Q 10 | 0.05 |
| Cetyl PG hydroxyethyl palmitamide | 0.20 |
| Paraffin oil (Paraffinum perliquidum, DAB 9) | 11.50 |

The powder was prepared by spraying the paraffin oil onto the basic powder mass in a fluidizing bed generator at about 20° C.

A dust-free powder is obtained, which shows good capability of being mixed with a known 6% $H_2O_2$ solution in a weight proportion of 1:1.

99% of the particles had a diameter of <400 microns.

The bleaching effect, gloss and elasticity of the hair are excellent with good wet and dry combability, there was no evidence of essential hair damage.

Omission of the Coenzyme Q 10 and cetyl PG hydroxyethyl palmitamide led to a reduced and less even bleaching effect; the hair showed a rougher texture and reduced wet and dry combability, and without elasticity. Hair showed compared to the inventive compostion significantly less volume.

EXAMPLE 4

| Dust-Free Bleaching Agglomerate | |
|---|---|
| Silicon dioxide (diatomaceous earth) | 3.20 (% by wt.) |
| Silicon dioxide (pyrogenic $SiO_2$) | 5.30 |
| Sodium carboxymethyl cellulose | 3.50 |
| Urea | 2.00 |
| Sodium lauroyl sarcosinate | 0.80 |
| Sodium stearate | 1.20 |
| Sodium carbonate | 1.00 |
| Sodium metasilicate | 6.00 |
| Starch powder | 4.40 |
| Sodium persulfate | 39.50 |
| Potassium persulfate | 14.02 |
| Magnesium peroxide | 4.00 |
| Cocomonoethanolamide | 15.00 |
| Cetyl PG hydroxyethyl palmitamide | 0.10 |
| Coenzyme Q 10 | 0.05 |
| Coenzyme Q 6 | 0.03 |

The powder was prepared by heating the above mixture to a temperature of 70° C. to 75° C. in a fluidizing bed generator and subsequent cooling.

A dust-free powder was obtained, which had good capability of being mixed with a known 9% $H_2O_2$ solution in a weight proportion of 1:1.5.

99% of the particles had a diameter of <400 microns.

The bleaching effect achieved on the hair was even and excellent with good wet and dry combability of the hair; substantial hair damage was not in evidence.

Omission of the coenzymes Q 10 and Q 6 and cetyl PG hydroxyethyl palmitamide led to a reduced conditioning and bleaching effect. The hair treated with this bleaching agent was dull and did not have any strength, elasticity.

EXAMPLE 5

| Dust-free Bleaching Powder | |
|---|---|
| Pyrogenic silica (aerosil) | 4.00 (Parts by wt.) |
| Hydroxyethyl cellulose | 1.70 |
| Polyvinyl pyrrolidone | 4.00 |
| Tetrasodium-EDTA | 2.00 |
| Sodium stearate | 1.25 |
| Sodium carbonate | 1.00 |
| Ammonium persulfate | 8.00 |
| Magnesium peroxide | 10.00 |
| Potassium persulfate | 44.00 |
| Sodium metasilicate | 11.50 |
| Sodium lauryl sulfate | 0.50 |
| Organopolysiloxane graft copolymer | 1.00 |
| Coenzyme Q 10 | 0.05 |
| Cetyl PG hydroxyethyl palmitamide | 0.20 |
| Paraffin oil, sprayed | 11.00 |

The powder was mixed with an aqueous 6% $H_2O_2$ composition in a proportion of 1:1 and the mixture was applied onto the hair. After completed processing, washing and drying, the hair thus treated showed good and even bleaching with unobtrusive gloss, soft texture and good wet and dry combability.

Omission of the coenzymes Q 10 and Q 6 and cetyl PG hydroxyethyl palmitamide led to a reduced conditioning and bleaching effect. The hair treated with this bleaching agent was dull and did not have any strength, elasticity.

EXAMPLE 6

| Bleaching powder | |
|---|---|
| Cetyl PG hydroxyethy palmitamide | 0.10 |
| Silica | 2.00 |
| Hydroxyethycellulose | 3.00 |
| Tetrasodium EDTA | 0.20 |
| Sodium stearate | 1.30 |
| Sodium carbonate | 0.90 |

-continued

| Bleaching powder | |
| --- | --- |
| Ammonium persulfate | 18.00 |
| Potassium persulfate | 40.00 |
| Sodium metasilicate | 11.50 |
| Sodium laurylsulfate | 0.50 |
| Mineral oil (Paraffinum liquidum) | 9.00 |
| Ubichinone 50 (Coenzyme Q10) | 0.05 |
| Diatomaceous earth | to 100.00 |

The powder was mixed with an aqueous 6% $H_2O_2$ composition in a proportion of 1:1 and the mixture was applied onto the hair. After completed processing, washing and drying, the hair thus treated showed good and even bleaching with unobtrusive gloss, soft texture and good wet and dry combability.

Omission of the coenzymes Q 10 and cetyl PG hydroxyethyl palmitamide led to a reduced conditioning and bleaching effect. The hair treated with this bleaching agent was dull and did not have any strength, elasticity.

EXAMPLE 6

| Bleaching powder | |
| --- | --- |
| Cetyl PG hydroxyethy palmitamide | 0.10 |
| Silica | 2.00 |
| Starch | 1.00 |
| Hydroxyethycellulose | 3.00 |
| Tetrasodium EDTA | 0.20 |
| Sodium stearate | 1.30 |
| Sodium carbonate | 0.90 |
| Sodium persulfate | 5.00 |
| Ammonium persulfate | 13.00 |
| Potassium persulfate | 40.00 |
| Sodium metasilicate | 11.50 |
| Sodium laurylsulfate | 0.50 |
| Mineral oil (Paraffinum liquidum) | 9.00 |
| Lipogard (1) | 1.00 |
| Diatomaceous earth | to 100.00 |

(1) Lipogard is trademark from Pentapharm Ltd and a mixture squalen, Ubichinone and Tocopheryl acetate.

The powder was mixed with an aqueous 6% $H_2O_2$ composition in a proportion of 1:1 and the mixture was applied onto the hair. After completed processing, washing and drying, the hair thus treated showed good and even bleaching with unobtrusive gloss, soft texture and good wet and dry combability.

Omission of the Lipogard and cetyl PG hydroxyethyl palmitamide led to a reduced conditioning and bleaching effect. The hair treated with this bleaching agent was dull and did not have any strength, elasticity.

The invention claimed is:

1. Water-free composition for the bleaching of human hair, comprising
   a) at least one compound with a bleaching or brightening effect, and
   b) 0.001% to 10%, calculated to the total composition, of at least one ubiquinone of the formula (I)

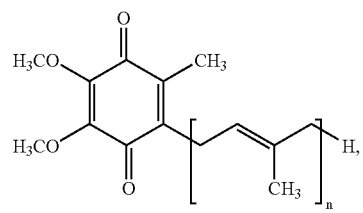

(I)

wherein n is a number from 1 to 10, and
   c) 0.001% to 10%, calculated to the total composition, of at least one sphingolipid of the formula (II)

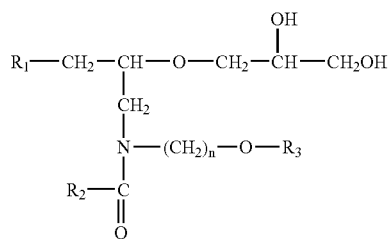

where $R^1$ and $R^2$ are independent from each other alkyl- or alkenyl group mit 10 to 22 carbon atoms, $R^3$ is methyl, ethyl, n-propyl or isopropyl group and n is a number between 1 to 6, preferably 2 or 3.

2. Composition according to claim 1, wherein n in the formula I is 10.

3. Composition according to claim 1, wherein n in the formula I is 6.

4. Composition according to claim 1, comprising 0.01% to 2.5% by weight, calculated to the total composition, of at least one ubiquinone.

5. Composition according to claim 1, comprising 0.01% to 2.5% by weight, calculated to the total composition, of at least one compound according to formula II.

6. Composition according to claim 1, comprising at least one peroxide as a compound with a bleaching and/or brightening effect.

7. Composition according to claim 1, comprising at least one ammonium salt as compound with a bleaching and/or brightening effect.

8. Process for the bleaching of human hair, wherein a water-free composition (A), comprising at least one bleaching or brightening compound, is mixed with an aqueous hydrogen peroxide composition (B), comprising 0.001% to 10% by weight, calculated to the total composition, of at least one ubiquinone of the formula (I)

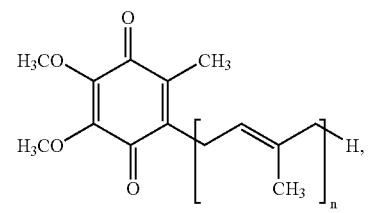

(I)

wherein n is a number from 1 to 10, and
at least one sphingolipid of the formula II

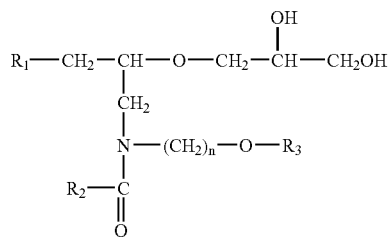

where $R^1$ and $R^2$ are independent from each other alkyl- or alkenyl group mit 10 to 22 carbon atoms, $R^3$ is methyl, ethyl, n-propyl or isopropyl group and n is a number between 1 to 6, preferably 2 or 3,
and the mixture is applied onto human hair.

* * * * *